US012588868B2

(12) United States Patent
Mattmueller

(10) Patent No.: US 12,588,868 B2
(45) Date of Patent: Mar. 31, 2026

(54) BIPOLAR MAPPING SUCTION DEVICE

(71) Applicant: inomed Medizintechnik GmbH, Emmendingen (DE)

(72) Inventor: Rudi Mattmueller, Emmendingen (DE)

(73) Assignee: INOMED MEDIZINTECHNIK GMBH, Emmendingen (DE)

( * ) Notice: Subject to any disclaimer, the term of this patent is extended or adjusted under 35 U.S.C. 154(b) by 270 days.

(21) Appl. No.: 17/765,836

(22) PCT Filed: Oct. 15, 2020

(86) PCT No.: PCT/EP2020/078984
§ 371 (c)(1),
(2) Date: Mar. 31, 2022

(87) PCT Pub. No.: WO2021/074265
PCT Pub. Date: Apr. 22, 2021

(65) Prior Publication Data
US 2022/0400972 A1 Dec. 22, 2022

(30) Foreign Application Priority Data

Oct. 18, 2019 (DE) .......................... 102019216119.7

(51) Int. Cl.
*A61B 5/0537* (2021.01)
*A61B 5/00* (2006.01)
(Continued)

(52) U.S. Cl.
CPC .......... *A61B 5/4848* (2013.01); *A61B 5/0537* (2013.01); *A61B 5/061* (2013.01);
(Continued)

(58) Field of Classification Search
CPC ......... A61B 5/0059; A61B 5/24; A61B 5/395; A61B 5/6852; A61B 5/4836; A61B 1/015;
(Continued)

(56) References Cited

U.S. PATENT DOCUMENTS

| | | | |
|---|---|---|---|
| 4,573,979 A | 3/1986 | Blake | |
| 5,458,597 A | 10/1995 | Edwards et al. | |

(Continued)

FOREIGN PATENT DOCUMENTS

| | | |
|---|---|---|
| CN | 101588765 A | 11/2009 |
| CN | 107920851 A | 4/2018 |

(Continued)

OTHER PUBLICATIONS

Decision to Grant a Patent for Japanese Patent Application Serial No. 2022-520317 (Sep. 28, 2023).

(Continued)

*Primary Examiner* — Deborah L Malamud

(74) *Attorney, Agent, or Firm* — Jenkins, Taylor & Hunt, P.A.

(57) ABSTRACT

A bipolar mapping suction instrument and a system for suctioning fluids and tissue and for monitoring nerve tissue are provided. The suction instrument includes a cannula unit, including electrically conductive inner and outer cannula tubes and insulation. The electrically conductive inner cannula tube is arranged concentrically in the outer cannula tube which can be insulated from the exterior. The electrically conductive inner cannula tube is mechanically connected to a handpiece and/or a first interface. The electrically conductive inner and outer cannula tubes are respectively electrically connected to first and second poles of a bipolar electrical connection of a second interface. The insulation is concentrically arranged between the outer cannula tube and (Continued)

the inner cannula tube and electrically isolates the outer cannula tube from the inner cannula tube.

17 Claims, 5 Drawing Sheets

(51) Int. Cl.

| | |
|---|---|
| *A61B 5/06* | (2006.01) |
| *A61B 5/294* | (2021.01) |
| *A61M 1/00* | (2006.01) |

(52) U.S. Cl.
CPC ............. *A61B 5/294* (2021.01); *A61M 1/774* (2021.05); *A61M 1/772* (2021.05)

(58) Field of Classification Search
CPC .......... A61B 5/00; A61N 1/3787; A61N 1/00; A61N 1/18; A61N 1/3603; A61M 25/00; A61M 1/71; A61M 1/74; A61M 1/75; A61M 2205/054; A61M 1/774; A61M 1/80

See application file for complete search history.

(56) References Cited

U.S. PATENT DOCUMENTS

| | | | | |
|---|---|---|---|---|
| 5,520,685 | A | 5/1996 | Wojciechowicz | |
| 5,861,002 | A | 1/1999 | Desai | |
| 5,925,045 | A | 7/1999 | Reimels et al. | |
| 2010/0331883 | A1* | 12/2010 | Schmitz ......... | A61B 17/320758 606/279 |
| 2014/0066930 | A1 | 3/2014 | Mark et al. | |
| 2014/0249542 | A1 | 9/2014 | Moffitt et al. | |
| 2017/0042528 | A1 | 2/2017 | Ellegala | |

FOREIGN PATENT DOCUMENTS

| | | |
|---|---|---|
| DE | 10 2010 019 796 A1 | 11/2011 |
| DE | 20 2014 000 600 U1 | 7/2014 |
| EP | 3158960 A1 | 10/2015 |
| EP | 3560528 A1 | 10/2019 |
| JP | 2014-226257 A | 12/2014 |
| KR | 1020170133499 A | 12/2017 |
| KR | 102119073 B1 | 6/2020 |
| RU | 183278 U1 | 9/2018 |
| WO | WO 2018/030393 A1 | 2/2018 |

OTHER PUBLICATIONS

Notice of Reasons for Refusal for Japanese Patent Application Serial No. 2022-520317 (Mar. 30, 2023).

International Search Report for International Application Serial No. PCT/EP2020/078984 (Feb. 1, 2021).

Seidel et al., "Continuous dynamic mapping to avoid accidental injury of the facial nerve during surgery for large vestibular schwannomas," Neurosurgical Review, vol. 43, pp. 1-8 (2020).

Raabe et al., "Continuous dynamic mapping of the corticospinal tract durin surgery of motor eloquent brain tumors: evaluation of a new method," J Neurosurg, pp. 1-10 (Mar. 14, 2014).

"Physik A—VL29," Elecktrostatik II—Felder, elektrische Arbeit und Potential, elektrischer Fluss, pp. 1-22 (Dec. 20, 2012).

International Search Report for Russian Patent Application Serial No. 2022108859 (Apr. 27, 2023).

Kartush, et al., "Intraoperative Facial Nerve Monitoring: A Comparison of Stimulating Electrodes", Laryngoscope 95, pp. 1536-1540 (1985).

Third Office Action for German Patent Application Serial No. 10 2019 216 119.7 (Mar. 3, 2023).

Second Office Action for German Patent Application Serial No. 10 2019 216 119.7 (May 25, 2022).

Office Action for German Patent Application Serial No. 10 2019 216 119.7 (Jul. 13, 2020).

Office Action for Russian Patent Application Serial No. 2022108859 (Apr. 27, 2023).

Office Action for Korean Patent Application Serial No. 10-2022-7011736 (May 9, 2025).

Office Action for Chinese Patent Application Serial No. 202080072097.0 (May 20, 2025).

Notice of Rejection for Japanese Patent Application Serial No. 2020520317 (Apr. 4, 2023).

Notice of Allowance for Korean Patent Application Serial No. 10-2022-7011736 (Jan. 6, 2026).

Notice of Allowance for Chinese Patent Application Serial No. 202080072097.0 (Jan. 13, 2026).

* cited by examiner

BIPOLAR MAPPING SUCTION DEVICE

FIELD OF THE INVENTION

The present invention relates to a suction instrument, in particular a bipolar mapping suction device, for surgical purposes, and to a system for suctioning fluids and tissues and for monitoring nervous tissue.

TECHNICAL BACKGROUND

Surgical procedures on the human body, such as tumor resections, involve a high risk of unintended nerve damage, depending on the surgical site. Especially during operations near important functional centers and nerves, it is particularly important not to injure nerve tissue in order to avoid movement, sensory and autonomic, as well as psychological disorders of the patient.

Intraoperative neuromonitoring is an established method for monitoring nerve tissue and can be used, for example, during tumor resection (e.g., in the brain). Interventions in which the tumor is directly adjacent to nerve tissue, such as a nerve or nerve pathway, are particularly risky. In order to spare this nerve tissue as much as possible during surgical interventions and to identify the pathway of the nerve tissue, intraoperative neuromonitoring is used in clinical practice. Here, the tissue to be examined is stimulated and it is checked whether a stimulus response is detected. To do this, a surgeon or another member of the surgical staff places a stimulation probe or stimulation electrode on the tissue during the procedure and stimulates it, for example electrically. At the same time, an evoked potential, for example an electromyogram (EMG), is usually derived from the patient via conductive electrodes, for example needle electrodes or surface electrodes, and the response signal is presented to the surgeon on a nerve monitor for interpretation. Thus, it can be determined whether or not healthy tissue is involved. To identify the nerve pathway, the surgeon scans the surgical area with the stimulation probe. In addition, based on stimulation intensities used, distances to motor pathways can be estimated. Differentiating between healthy and tumorous tissue allows for more effective tumor resection.

In addition, during a surgical procedure, regardless of the location of a tumor, the situs must be as free of (body) fluids as possible to avoid obstructing the surgeon's view. For the surgeon's or operator's unobstructed view of the situs, it should be as free as possible from fluids such as blood or other body fluids. This enables the surgeon to identify tissue that needs to be spared at an early stage.

For example, in tumor resections, depending on the tumor and surgical site, the procedure is performed minimally invasively through a small skin incision or through natural body orifices. In addition, for large tumors, "open" surgery with a large skin incision may be necessary. The selection of the appropriate surgical technique depends on the location and extent of the tumor, although all methods have the goal of removing the tumor as extensively as possible without affecting nerve tissue and its function.

Based on this, the goals are therefore to aspirate tumor tissue and fluids on the one hand, and at the same time to continuously localize nerve tissue and monitor its function during the procedure (e.g., tumor resection) to avoid nerve damage with possible consequences for the patient. It is desirable to have an instrument that continuously stimulates the tissue and provides feedback to the operator whether it is tissue that needs to be removed or not. At the same time, nerve tissue and its course should be identified and spared.

(Body) fluids should be able to be aspirated at any time, giving the user an unrestricted view of the dry situs.

To achieve both goals, special suction devices are used that can both aspirate fluids, such as blood or irrigation medium, as well as electrically stimulate the tissue. In monopolar suction devices, only one stimulation pole is located on the suction device itself. At least one additional counter electrode (e.g., needle electrode or surface electrode) is attached as a second pole. The placement of needle electrodes generally carries the risk of bleeding, which is why a more patient-friendly method is desirable. Additionally, with this method, the distance between the two stimulation poles is large, and therefore only highly sensitive, but not selective, measurement is possible.

This is a condition that needs to be improved.

SUMMARY OF THE INVENTION

In view thereof, there is a need to combine the intraoperative neuromonitoring with the resection of tissue or removal of fluids from the situs, and also to eliminate or at least to alleviate disadvantages of the prior art.

According to the invention, this object is solved by a suction device, in particular a bipolar mapping suction device, for surgical purposes with the features described herein and/or a system for aspirating fluids and tissue and for monitoring nerve tissue with the features of such a system described herein. Further embodiments are the subject of the corresponding dependent patent claims.

The suction device and the system according to the present invention are suitable for monopolar or bipolar stimulation of tissue of any kind for differentiation between tumorous and healthy tissue and for localization of surrounding nerve tissue and the pathway thereof, as well as for parallel or sequential suction of tissue and fluids such as blood. Thus, nerve damage during a surgical procedure can be avoided.

According to a first aspect of the present invention, a suction device, in particular a bipolar mapping suction device, for surgical purposes, comprises a handpiece, a first interface, a second interface and a cannula unit. The first interface is configured to establish at least one fluid connection with an external suction device, and additionally or alternatively with a rinsing device. The second interface is configured to establish a bipolar electrical connection with an external stimulation device. The cannula unit extends from the handpiece in an axial direction and is mechanically connected to the handpiece at a proximal end of the cannula unit. The cannula unit includes an electrically conductive outer cannula tube, an electrically conductive inner cannula tube, and insulation. The electrically conductive inner cannula tube is electrically connected to a first pole of the bipolar electrical connection of the second interface. The electrically conductive inner cannula tube is concentrically disposed within the outer cannula tube. The electrically conductive inner cannula tube is fluidly connected to the first interface. The electrically conductive outer cannula tube is electrically connected to a second pole of the bipolar electrical connection of the second interface. The insulation is concentrically disposed between the outer cannula tube and the inner cannula tube. The insulation is configured to fully electrically isolate the outer cannula tube and the inner cannula tube in relation to one another.

According to a second aspect of the present invention, a system for suctioning fluids and tissue and additionally or alternatively irrigating a situs and monitoring nerve tissue comprises the suction instrument according to the first aspect of the present invention, a suction device and additionally or alternatively an rinsing device, at least one, preferably two, conductive electrodes, and an intraoperative neuromonitoring (IOM) system. The at least one, preferably two, conductive electrodes are attachable to a patient in the vicinity of nerve tissue to be monitored. The IOM system includes a stimulation device and a monitoring device. The monitoring device is communicatively connected to the stimulation device. The suction device and additionally or alternatively the rinsing device is fluidly connected to the suction device by means of a fluid line, in particular a semirigid tube, via the first interface. The stimulation device of the IOM system is electrically connected by means of a monopolar or alternatively a bipolar connection, in particular a monopolar or alternatively bipolar cable, to the suction device via the second interface in a monopolar or alternatively bipolar manner. The stimulation device is configured to electrically stimulate tissue via at least one of the two cannula tubes (monopolar stimulation), and additionally or alternatively via both cannula tubes (bipolar stimulation). The monitoring device is electrically connected to the at least one, preferably at least two, conductive electrodes and is configured to monitor a stimulus response recorded by the conductive electrodes (for example, needle electrodes or surface electrodes), and to additionally or alternatively output it to a user acoustically and additionally or alternatively visually.

In the context of the present invention, the term fluid-conducting is understood to mean that a liquid or gaseous fluid can be conveyed tightly along a fluid-conducting conduit or across a fluid-conducting interface. In this context, the term tight is understood to mean that no leakage can occur that would interfere with the operation of the suction device.

In the context of the present invention, the term electrical is understood to mean that both an electrical current and information can be transmitted via an electrical connection or via an electrical interface. In this context, an electrical line or connection or an electrical interface can have several electrical lines or electrical connections or electrical contacts (e.g. plugs or sockets) by which information can be transmitted not only serially but also in parallel.

In the following, the terms "proximal" and "distal" are used in the following way: The definitions are seen in relation to the user. "Distal" means the end that is further away from the user (towards a tip of the suction device). Accordingly, "proximal" means the end that is closer to the user (in this case, the handpiece which the user is holding).

In the present context, surgical purposes are all purposes for which the suction device can be used in the context of a surgical procedure, for example a minimally invasive tumor resection.

The handpiece is used by the user, for example a surgeon, to handle the suction device. The user can hold and guide the suction device by the handpiece. The handpiece may preferably be made of a plastic material. In addition, the handpiece may be particularly preferably ergonomically shaped so that it rests in the hand of the user while the user guides the suction device.

The handpiece is mechanically connected to the cannula unit. The handpiece and cannula unit are preferably firmly connected to each other, so that a rotation or translation against each other is not possible. The handpiece and the cannula unit can be mechanically connected to each other by means of positive locking and additionally or alternatively by means of frictional locking and additionally or alternatively by means of material locking. In particular, the outer cannula tube of the cannula unit and additionally or alternatively the inner cannula tube of the cannula unit may be mechanically connected to the handpiece for this purpose, in order to provide the mechanical connection between the cannula unit and the handpiece.

The first interface is used to connect the external suction device and additionally or alternatively the external rinsing device to the suction instrument. The first interface may be of standardized design for this purpose. The first interface can be configured in the form of a spigot or several spigots to which, for example, a semirigid tube with one fluid line or a semirigid tube in which two fluid lines are integrated or two separate semirigid tubes can be connected. By means of the first interface, a fluid-conducting connection is established between the inner cannula tube, more precisely an inner lumen of the inner cannula tube, and the suction device and additionally or alternatively the rinsing device.

The first interface may be arranged on the handpiece or alternatively on the cannula unit. If the first interface is arranged on the cannula unit, then the first interface is directly fluidly connected to the inner cannula tube of the cannula unit or its lumen. If the first interface is arranged on the handpiece (for example, at a proximal end of the handpiece or behind a grip surface of the handpiece), then the first interface is mechanically connected (e.g., by means of a connector) to the handpiece. Alternatively, the handpiece and the first interface may be of one-piece or integral design. Further, the first interface is fluidly connected to the inner cannula tube by means of one or more fluid channels in the handpiece. For this purpose, the handpiece can be hollow in its interior, for example, and establish the fluid-conducting connection between the first interface arranged on the handpiece in this example and the inner cannula tube or its lumen by means of this hollow space. The fluid channel(s) (e.g., the cavity inside) of the handpiece are fluidly and tightly connected to the inner cannula tube.

Thus, a negative pressure or vacuum can be provided by means of the first interface from the connected suction device, which can be used to aspirate fluids such as blood and tissue, such as tumor tissue from the situs (surgical site). Additionally or alternatively, an irrigation medium such as isotonic saline solution can be provided at a predetermined pressure by means of the first interface from the connected rinsing device so that the situs can be irrigated. If the suction device and the rinsing device are connected together to the suction device by means of the first interface in a fluid-conducting manner, the tissue can be moistened and cleaned by means of the rinsing medium from the rinsing device and adhesions can be loosened and the rinsing medium as well as blood and tissue can be suctioned off by means of the negative pressure of the suction device.

The second interface is used to connect the external stimulation device. The interface can be standardized for this purpose, for example in accordance with DIN 42802 (touch-proof-plug/socket). The second interface can be configured in the form of one or more plugs or one or more sockets. A plug can have several pins, and a socket can have several receptacles for pins. A corresponding cable can be connected to the second interface. Alternatively, the second interface itself may comprise at least one, in particular two or more such cables. By means of the second interface, an electrical connection is established between the inner cannula tube and additionally or alternatively between the outer cannula tube and the stimulation device.

The second interface may be arranged on the handpiece, or alternatively on the cannula unit. When the second interface is arranged on the cannula unit, the first pole of the bipolar electrical connection of the second interface is electrically connected directly to the inner cannula tube of the cannula unit and the second pole of the bipolar electrical connection of the second interface is electrically connected to the outer cannula tube of the cannula unit. When the second interface is arranged on the handpiece (for example, at a distal end of the handpiece or in front of a gripping surface of the handpiece), the first pole of the bipolar electrical connection of the second interface is electrically connected to the inner cannula tube by means of a first electrical lead in or on the handpiece, and the second pole of the bipolar electrical connection of the second interface is electrically connected to the outer cannula tube by means of a second electrical lead in or on the handpiece. For example, the first and second electrical leads in or on the handpiece may be a combined electrical lead.

Thus, by means of the second interface, an electric current with an electric voltage can be provided by the connected stimulation device at one of the two poles, and thus at the inner cannula tube (first pole) or the outer cannula tube (second pole) or, alternatively, between both poles, and thus between the inner and outer cannula tubes, with which tissue, in particular nerve tissue, can be electrically stimulated.

A stimulus response of the stimulated (nerve) tissue can then be recorded by means of the conduction electrodes (for example, needle electrodes or surface electrodes) attached to the patient in the vicinity of the nerve tissue to be monitored and electrically transmitted to the electrically connected monitoring device for further analysis.

The outer cannula tube is configured to be electrically conductive so that it can serve as an electrode for stimulating (nerve) tissue, or, alternatively, for recording or detecting the stimulus response of the stimulated tissue. The outer cannula tube can be electrically insulated from the environment (e.g., coating of an electrically insulating plastic/polymer, lacquer, or ceramic). However, this is not absolutely necessary in the case of bipolar stimulation, because in this case the current only flows between the two stimulation contacts, i.e. from the inner cannula tube to the outer cannula tube, or vice versa. If monopolar stimulation is performed by means of the inner cannula tube and a separate counter-electrode (e.g. needle electrode or surface electrode) that has been attached to the patient at a suitable location, there may be insulation of the outer cannula tube from the outside. In the case of monopolar stimulation by means of the outer cannula tube and the counter-electrode, on the other hand, there must be insulation of the outer cannula tube from the outside, so that the current is delivered and thus the tissue is stimulated only by means of the tip of the cannula unit and not already at the shaft or outer surface of the outer cannula tube.

The inner cannula tube is also configured to be electrically conductive so that it can serve as an electrode for stimulating tissue or, alternatively, for recording or detecting the stimulus response of stimulated tissue. The inner cannula tube is concentrically disposed within the outer cannula tube and extends from a proximal end of the outer cannula tube to the tip (distal end) of the outer cannula tube. Inside the inner cannula tube extends a lumen capable of conducting fluid, tissue, or gases. The inner cannula tube may extend from the proximal end of the outer cannula tube, thereby extending into the interior of the handpiece.

The interior of the handpiece may be empty (hollow) or may be divided into, for example, two cavities extending parallel to each other, for example, by a partition wall extending axially in the handpiece, to the beginning of the inner cannula tube. The cavities represent separate fluid lines for fluids or for the negative pressure and the rinsing medium. One cavity may be fluidly connected to the suction device by means of the first interface and optionally by means of a corresponding fluid line in the handpiece. The other cavity may be fluidly connected to the rinsing device by means of the first interface and optionally by means of a corresponding fluid line in the handpiece.

The isolation is arranged between the outer and inner cannula tubes. The insulation may be formed as a one-piece tube extending concentrically along both cannula tubes and electrically insulating an inner tube surface of the outer cannula tube from an outer tube surface of the inner cannula tube to prevent an electrical short. The insulation may also be formed as one or more spacers (e.g., rings) that prevent contact between the inner tube surface of the outer cannula tube and the outer tube surface of the inner cannula tube, thereby preventing an electrical short. The electrical isolation of the two cannula tubes allows them to be used as stimulation electrodes in the stimulation of (nerve) tissue.

In addition to the suction instrument described above, the system also comprises the suction device and additionally or alternatively the rinsing device, each of which is fluidly connected to the suction instrument by means of the fluid line (semirigid tube) connected to the first interface, the at least one, preferably two, conductive electrodes, and the IOM system.

The IOM system comprises the stimulation device, which is connected in a monopolar or alternatively bipolar way to the second interface by means of the monopolar or alternatively bipolar connection (cable), and is thus connected in a monopolar or alternatively bipolar way to the outer cannula tube and the inner cannula tube of the cannula unit of the suction device accordingly. In addition, the IOM system also comprises the monitoring device, which is communicatively connected to the stimulation device, for example by means of a wiring or bus system.

For bipolar stimulation, the stimulation device can electrically stimulate tissue by means of both cannula tubes. For monopolar stimulation, the stimulation device can electrically stimulate tissue by means of one of the two cannula tubes, but preferably by means of the inner cannula tube due to the more area-focused excitation and isolation. Furthermore, a counter electrode (needle electrode or surface electrode) is placed on the patient to enable monopolar stimulation. The stimulus response of the stimulated tissue can be recorded or derived by means of the at least one, preferably two, conductive electrodes of the system. The recorded stimulus response of the monopolar or alternatively bipolar stimulated tissue (nerve tissue) can be recorded as a detection signal by the monitoring device, additionally or alternatively amplified and filtered. Subsequently, the monitoring device provides the, optionally amplified or filtered stimulus response or detection signal. The user, for example the surgeon, monitors the stimulus response or detection signal (e.g., estimating distances to nerve tissue, etc.), with the signal being displayed, for example, visually or acoustically, for example, on a monitor. Alternatively or additionally, the monitoring device outputs the stimulus response or the detection signal to the user visually (e.g. by means of a monitor on which the course of the stimulus response or the detection signal is displayed graphically) or acoustically (e.g. by means of a signal tone whose volume increases with decreasing distance to nerve tissue). In both stimulation variants, the stimulus response recorded by means of the conductive electrodes can be recorded as an evoked potential and thus as a conductive signal by the monitoring device, additionally or alternatively amplified and/or filtered. Subsequently, the monitoring device provides the, optionally filtered or amplified, stimulus response or the derivative signal, for example, visually on a monitor or tablet for analysis and monitoring. Alternatively or additionally, the monitoring device acoustically outputs (e.g., by a beep) the tissue stimulation and/or the EMG signal to the user by means of a speaker.

Thus, the present invention provides a suction instrument and a system comprising the same that electrically stimulates tissue by means of the two nested cannula tubes. The suction device can aspirate tumor tissue as well as fluids so that the user (e.g., surgeon) can achieve an unobstructed view of the situs. By means of the alternative or additional irrigation function, the situs can also be rinsed, prevented from drying out, and adhesions or dried surgical residues can be loosened. This enables reliable differentiation between tumorous and healthy tissue as well as nerve localization in the tissue and thus a patient-friendly resection. The suction instrument or bipolar mapping suction device and the system according to the present invention can be used, for example, for patient-sparing tumor resection. The combination of a surgical suction device and a bipolar stimulation probe implemented by the suction device enables suction of tumor tissue and fluids in situs during tumor resection, for example on the peripheral and central nervous system, and at the same time continuous, dynamic identification (mapping) of nerve tissue, for example of the motor pathways of the central nervous system (pyramidal pathway). The main advantage of the present invention is that it is no longer necessary to awkwardly switch between stimulation probe or stimulation electrode to a suction instrument or irrigation instrument, or to use both instruments simultaneously in situs. In particular, bipolar stimulation, i.e. stimulation of the tissue by means of both cannula tubes, has the advantage that it is no longer necessary to attach a second electrode as a counter-electrode (needle electrode or surface electrode) for stimulation on the patient. The current flows in a more controlled manner between the two predefined electrode contacts (inner and outer cannula tubes) and does not spread into the surrounding tissue, allowing very focused stimulation and detailed examination of the tissue.

Thus, bipolar stimulation or monopolar stimulation of the tissue can be performed as needed, and the optimal type of stimulation can be applied during the surgical procedure.

Advantageous embodiments and further embodiments result from the further dependent claims as well as from the description with reference to the figures of the drawings.

According to a further embodiment of the present invention, the suction instrument further comprises an illumination device. The illumination device comprises a light outlet, a light guide and, additionally or alternatively, a light source. The light outlet is arranged on the handpiece or alternatively on the cannula unit, and is configured to allow light to exit from the light guide or alternatively from the light source in the direction of a situs. The light guide is configured to direct light emitted from the light source, or alternatively from an external light source, to the light outlet.

The light outlet is arranged either in the region of the tip of the cannula unit or at a distal end of the handpiece. The light outlet may include a lens for focusing or diffusing emitted light. The light outlet may emit light directly from a light source, such as a light source arranged at the distal end of the handpiece. Alternatively, the light outlet may emit light that has been directed from the light source or external light source to the light outlet by means of the light guide.

The light guide may be, for example, an optical fiber or a bundle of optical fibers along which light from the (external) light source may be guided. For example, the light guide may extend from the proximal end of the cannula unit to the tip (distal end) thereof and direct light from a light source arranged at the exemplary distal end of the handpiece to the tip of the cannula unit. The light guide may extend along an outer tube surface of the outer cannula tube. Alternatively, the light guide may extend along the inner tube surface of the outer cannula tube, wherein the light guide may be embedded in the insulation and optionally may extend along the outer tube surface of the inner cannula tube. Further alternatively, the light guide may extend along the outer tube surface of the inner cannula tube, wherein the light guide may be embedded in the insulation. Also alternatively, the light guide may extend along the inner tube surface of the inner cannula tube. Alternatively, the light guide may extend from an external light source through the handpiece and/or cannula unit to the light outlet, thereby directing externally generated light to the light outlet.

The light guide is optically connected to the light source or external light source. Either the light source is encompassed by the suction instrument and integrated into the handpiece, for example, or it is an external light source. The external light source may be a stand-alone external device or may be encompassed by an external device, for example, the stimulation device or the IOM system. The light source encompassed by the suction instrument may be electrically powered, for example, by means of the second interface. The light source or the external light source may preferably be an LED. This may be electrically connected to a power source, wherein the power source is, for example, comprised by the stimulation device or the IOM system and supplies power to the LED. The LED may be integrated directly on or in the handpiece, preferably at its distal end. Alternatively, the LED may be arranged directly on the cannula unit.

With the light emitted directly from the light source or from the light guide at the light outlet, the situs can be better illuminated, so that the user or surgeon has an improved view of the structures and tissues arranged in the situs, and can better differentiate them.

In accordance with a further aspect of the present invention, the suction instrument further comprises a tracking element. The tracking element is configured to be detected by an external navigation device. The tracking element is fixedly or releasably mechanically connected to the handpiece or cannula unit.

The tracking element may be an active element (e.g., light emitting diodes, electromagnetic element), or may be a passive tracking element (e.g., optical markers). The tracking element comprises, at least one, preferably three (active or passive) markers arranged in a predefined geometry with respect to each other (e.g., three tracking spheres arranged in a predefined uneven triangle on the tracking element). The markers can be detected in space by the navigation device (e.g., stereo camera, two electromagnetic sensors, etc.). From the location and pose (position and orientation) of the markers, the navigation system can indicate the relative position and pose of the suction instrument in relation to the patient and to registered patient image data.

The tracking element can be detachably mechanically connected to the handpiece or directly to the cannula unit, for example by screwing on or by a snap-on mechanism, or alternatively firmly or rigidly mechanically connected to the, for example, proximal end of the handpiece or to the cannula unit.

By means of the tracking element, the position and pose of the suction instrument in relation to the patient and in the registered image data of the patient can be displayed to the user or surgeon, whereby, even if the situs cannot be viewed from the outside, the position and pose of the tip of the suction instrument in the situs, i.e. within the patient, can be recognized by the user or surgeon.

According to a further embodiment of the present invention, the outer cannula tube and optionally the inner cannula tube and additionally or alternatively the insulation are biocompatible or bioinert. In particular, the outer cannula tube and additionally or alternatively the inner cannula tube are made of stainless steel, and additionally or alternatively the insulation is made of plastic, in particular polyamide.

The biocompatible design ensures that the few substances (e.g. ions) emitted by the outer cannula tube or the inner cannula tube or the insulation do not trigger a negative reaction (e.g. allergy, change in pH, poisoning, etc.) in the situs or the patient. The bioinert design ensures that no substances are released from the outer cannula tube or inner cannula tube or insulation into the situs.

According to a further embodiment of the present invention, the cannula unit has an outer diameter ranging from 1 mm [millimeter] to 15 mm.

Depending on the type of surgical procedure and location of the situs on the patient, different diameters of the cannula unit or outer cannula tube may be useful.

The outer cannula tube and additionally or alternatively the inner cannula tube may have a wall thickness of 1% [percent] to 10% of the outer diameter of the cannula unit. In this regard, the outer cannula tube and the inner cannula tube may have the same wall thickness, or each may have a different wall thickness.

The wall thickness allows the area of the outer and inner cannula tubes in contact with the tissue to be adjusted to the optimal electrical properties for stimulation of tissue and recording or detection of stimulus responses.

According to a further embodiment of the present invention, the cannula unit has a length of 10 cm [centimeters] to 40 cm.

Depending on the type of surgical procedure and location of the situs on the patient, different lengths of the cannula unit, i.e., the outer and inner cannula tubes, may be useful.

According to a further embodiment of the present invention, the cannula unit is straight, or has an angulation in a proximal region with an angle of 10° [degrees] to 60°, preferably of 30°.

Depending on the type of surgical procedure and the position of the situs on the patient, the cannula unit or the two cannula tubes may not only be straight but may be bent at an angle, preferably of 30°, at the proximal end near the handpiece so that the user's view of the structures and tissue in the situs is not impaired by his own hand.

According to a further embodiment of the present invention, the handpiece comprises a suction control orifice fluidly connected to the inner cannula tube.

The suction control orifice is fluidly connected to the lumen of the inner cannula tube by means of respective fluid lines in the handpiece. For example, the suction control orifice may be fluidly connected to the cavity in the handpiece that connects the first interface to the inner cannula tube or its lumen. In addition, the suction control orifice can be tightly closed by a finger, preferably the thumb, of the user. Alternatively, it is also possible to close the suction control opening with a (finger-actuated) slider or flap. Preferably, the suction control opening is arranged on an upper side of the handpiece.

If the suction control opening is free and not covered, the negative pressure or vacuum at the tip (distal end) of the cannula unit is reduced, which reduces the suction force. The further the suction control opening is closed (with the finger), the greater the suction force at the tip of the cannula unit becomes again. The suction control opening is thus used to control the suction intensity. During the suction process, the user can close the suction control opening (with the thumb) and increase the suction at the tip of the cannula unit accordingly. For example, if unwanted tissue (e.g., nerve tissue) is aspirated by the tip of the cannula unit during surgery, the suction at the tip can be reduced by opening the suction control opening (lifting the thumb) and the tissue at the tip falls off.

According to a further embodiment, the cannula unit is fixedly or releasably mechanically connected to the handpiece at the proximal end of the cannula unit.

For example, the cannula unit can be screwed into the handpiece or secured in or on the handpiece by means of a snap lock or a bayonet lock or a Luer lock, and can thus be detachably mechanically connected to it. Alternatively, the cannula unit can be firmly mechanically connected to the handpiece, for example by bonding or by being poured into the handpiece. If fluid lines and additionally or alternatively electrical lines for connecting the first and second cannula tubes to the first and second interfaces, respectively, are provided in the handpiece, corresponding seals or contacts are provided on the handpiece to ensure the fluid-conducting or electrical connections from the outer and inner cannula tubes to the first and second interfaces, respectively.

This has the advantage, especially if the first and second interfaces are arranged directly on the cannula unit, that the handpiece can be configured in a particularly simple manner (without electrical lines or fluid channels). In addition, existing standard handpieces can be retrofitted with the cannula unit according to the present invention. In addition, the handpiece and the cannula unit can be separated in relation to one another after the surgical procedure and then cleaned separately and, for example, the cannula unit can be sterilized on the one hand and the handpiece merely disinfected.

The suction instrument with its individual parts can be configured for single or multiple use. Consequently, the materials used for manufacturing are also intended for possible reprocessing with, for example, ethylene oxide.

According to a further embodiment of the present invention, the suction instrument further comprises a first controllable valve and a second controllable valve. The inner cannula tube is fluidly connected to the external suction instrument by means of the first controllable valve and a first fluid port of the first interface. Additionally or alternatively, the inner cannula tube is fluidly connected to the external rinsing device by means of the second controllable valve and a second fluid port of the first interface.

The controllable valves are configured as controllable check valves or flow control valves. Both controllable valves can either lock/unlock when at rest and release/open when actuated, or conversely release/open when at rest and lock/unlock when actuated. The controllable valves can be actuated mechanically (e.g., by means of a knob, a switch, a lever, a rotary tap, etc.) and additionally or alternatively electrically (by means of a circuit with appropriate wiring) and additionally or alternatively magnetically (integrated or external switchable electromagnet), i.e., movable from an open position to a closed position and vice versa.

By means of the first and second controllable valves, the suction device or the rinsing device can be selectively switched on or off, and thus the situs can be suctioned or flushed as required.

According to a further embodiment of the present invention, the handpiece further comprises a first operating element. The first operating element is configured to switch between a suction function of the external suction instrument and a rinsing function of the external rinsing device.

The first operating element is thereby configured to selectively switch between the suction function and the rinsing function, so that tissue or fluids can be suctioned or the situs can be rinsed, as required. By actuating the first operating element, the suction instrument is made usable either for aspirating fluid, tissue or gases or for rinsing the situs.

For this purpose, the suction instrument may comprise, for example, the first controllable valve and the second controllable valve. In this regard, the first operating element is configured to open the first controllable valve and simultaneously close the second controllable valve, as well as to close the first controllable valve and simultaneously open the second controllable valve. Optionally, the first operating element can additionally be configured to close both controllable valves.

Alternatively, the valves or a valve can be integrated, for example, at the fluid-conducting connection of the first interface to the suction instrument and/or rinsing device. Also alternatively, the external suction device and the external rinsing device can also be controlled, that is switched on and off, by means of the first operating element. For this purpose, the first operating element is communicatively connected, for example by means of the first or second interface, to the external suction device and/or the external rinsing device. In these exemplary embodiments, controllable valves in or on the handpiece can be dispensed with.

The first operating element can be configured, for example, as a switch on the handpiece or, alternatively, on the cannula unit, which mechanically controls the first controllable valve and the second controllable valve, for example, or communicatively controls the external suction device and the external rinsing device.

The user can operate the first operating element (switch) with a finger, for example. Preferably, the first operating element is arranged on a lateral surface of the handpiece and is operable with the thumb or the index finger.

The first operating element can be moved to a first position (e.g., switch flipped all the way up/right), and to a second position (e.g., switch flipped all the way down/left). In the first position, the first operating element can turn on the suction function and turn off the purge function, allowing fluid to be aspirated while preventing simultaneous purging of the situs.

This can be accomplished, for example, by turning on the external suction device and turning off the external rinsing device by the first operating element. Alternatively, the first operating element may open the first controllable valve and close the second controllable valve simultaneously. In the second position, the first operating element may turn off the suction function and turn on the flushing function, allowing flushing by means of flushing fluid while preventing simultaneous suction of the situs. This can be done, for example, by switching off the external suction device and switching on the external rinsing device by the first operating element. Alternatively, the first operating element can close the first controllable valve and open the second controllable valve simultaneously. Consequently, only one function can be performed at a time by operating the switch, either suction or rinsing.

Optionally, the first operating element can additionally be moved to a third position (e.g. switch toggled to a middle or neutral position). In the third position, the first operating element can turn off the external suction device and the external rinsing device, or alternatively close the first controllable valve and simultaneously close the second controllable valve. Neither suction nor irrigation is possible, so that only pure monopolar or bipolar stimulation can be performed by means of the suction instrument.

With the first operating element, the suction device and the rinsing device can be switched on and off, so that the situs can be either suctioned or rinsed (or neither) particularly easily and quickly.

According to a further embodiment of the present invention, the second interface comprises two connection pins for establishing the monopolar or bipolar connection. Alternatively, the second interface comprises a bipolar cable for making the monopolar or bipolar electrical connection.

The two connection pins are non-insulated, electrically conductive protrusions that may have a substantially cylindrical shape. Preferably, the two connection pins are touch proof connectors, which are particularly preferably configured according to DIN 42802. One of the two connection pins is provided for the first pole of the bipolar electrical connection and the other of the two connection pins is provided for the second pole of the bipolar electrical connection. Alternatively, a monopolar connection and thus monopolar stimulation are possible by connecting a monopolar cable to only one of the two connection pins, preferably to the first pole connected to the inner cannula tube of the cannula unit.

The two connection pins may be arranged on the handpiece, preferably on an underside of the handpiece and particularly preferably distally on the underside of the handpiece, and can be electrically connected to the inner cannula tube and the outer cannula tube by means of appropriate electrical connections, for example by means of solder joints or welds. Alternatively, the two connection pins can be arranged directly on the cannula, preferably on an underside of the cannula unit and particularly preferably proximally on the underside of the cannula unit and electrically connected directly to the inner cannula tube and the outer cannula tube. A cable can be connected to each of the two connection pins for bipolar stimulation or, alternatively, if monopolar stimulation is required, only one cable can be connected to a connection pin for electrical connection to the stimulation device.

The advantage here is that the suction instrument can be disconnected from the respective connection cable if required (e.g. cleaning and sterilization).

Instead of the two connection pins, a bipolar cable can be provided. The bipolar cable can have at its end, either two plugs or two pins in a common plug or two sockets or two receptacles for one pin each in a common socket, which are preferably touch-proof and particularly preferably configured according to DIN 42802. The bipolar cable is either connected directly to the handpiece, preferably to an underside of the handpiece, particularly preferably distally to the underside of the handpiece, and is electrically connected to the outer cannula tube and the inner cannula tube, for example, by means of appropriate electrical connections, for example by means of solder joints or welds. Or, alternatively, the bipolar cable is connected directly to the cannula unit, preferably to an underside of the cannula unit and particularly preferably proximally to the underside of the cannula unit and electrically connected directly to the outer cannula tube and the inner cannula tube. The stimulation device can be connected to the bipolar cable. If the bipolar cable is comprised of the second interface, then only one(s)

of two sockets or connectors of the bipolar cable can be plugged into the stimulation device to allow monopolar stimulation.

The advantage is that the cable does not have to be connected to the suction instrument before use, which saves time.

The two connection pins or the bipolar cable allow for particularly easy and quick electrical connection of the suction instrument to the stimulation device in a monopolar or bipolar fashion.

According to a further embodiment of the present invention, the suction instrument further comprises a second operating element. The second interface is further configured to establish a communicative connection of the second operating element with the external stimulation device. The second operating element is configured to switch between a monopolar operation and a bipolar operation.

The second operating element may be a switch or the like. The second operating element is movable to two or alternatively three positions (e.g., switch flipped fully up/right switch flipped fully down/left and switch flipped to a middle or neutral position). In the first position, the second operating element can communicate (e.g., rising edge, etc.) to the stimulation device by means of the second interface that bipolar operation is to be performed in which the tissue is stimulated by means of a current flow between the two cannula tubes. In the second position, the second operating element may communicate (e.g., falling edge, etc.) to the stimulation device by means of the second interface that monopolar operation is to be performed, in which one of the two cannula tubes stimulates tissue. In monopolar stimulation, an external counter electrode is attached to the patient near the (nerve) tissue to be stimulated and the electric current or voltage is applied between the corresponding cannula tube and the external counter electrode. The stimulus response of the bipolar or monopolar stimulated tissue is recorded or derived by means of additional conductive electrodes attached to the patient. In the third position of the second operating element, the stimulation device cannot stimulate (neither monopolar nor bipolar), so that only pure suction of tissue and fluid or irrigation of the situs is possible.

The second operating element can be used to switch between bipolar and monopolar operation as needed, so that the optimal mode can be quickly and easily selected by the user. Additionally, tissue stimulation can be quickly turned off completely.

In accordance with a further aspect of the present invention, the system either further comprises an impedance measurement device communicatively connected to the monitoring unit and configured to perform an impedance measurement, or alternatively, the IOM system is configured to perform the impedance measurement. Impedance measurement involves measuring complex resistances at various frequencies of tissue surrounding the tip of the cannula unit. The system, in particular the monitoring unit, is configured to determine the type of tissue based on the measured impedances and output it to the user.

It is possible to perform impedance spectroscopy by means of the cannula unit of the suction instrument. During a surgical procedure, the electrical impedance at different frequencies of the tissue surrounding the tip of the cannula unit can be measured to determine the type of tissue. This involves differentiation of, for example, bone, nerve tissue and/or skin, and preferably differentiation of tumor tissue and healthy tissue, for example in the brain. The impedance of the tissue is thereby measured, for example, within an annular volume at the uninsulated tip of the cannula unit, with the distribution of the current depending on the tissue properties. Alternating currents are introduced into the tissue with different, predefined frequencies. Depending on the respective frequency, different types of tissue each have a different impedance. The impedances at the different, predefined frequencies are characteristic for different types of tissue.

In impedance spectroscopy, an alternating electrical signal, for example a predefined alternating current or voltage, for example but not exclusively in the form of a square wave signal or a sinusoidal signal, is applied to the tissue by means of one of the cannula tubes at the tip of the cannula unit. The impedance meter or IOM system then correspondingly measures the voltage or current at the other cannula tube and calculates the impedance of the tissue by means of a corresponding signal processing chain and/or software.

The possibility of impedance spectroscopy by means of the suction instrument also eliminates the need to change instruments, as signal delivery is also by means of the system delivering the monopolar and/or bipolar stimulation. In a bipolar setup, the current or voltage path is advantageously concentrated in the area between the two stimulation poles, whereby the impedance measurement is largely influenced only by the local tissue, whereas in a monopolar setup, the current or voltage path is directed through tissue that is not relevant to the examination to a counter electrode (for example, needle electrode or surface electrode) attached to the patient, so that the measurement of impedance could be influenced.

The above embodiments and further embodiments can be combined with each other as desired, if useful. Other possible embodiments, further embodiments and implementations of the invention also comprise combinations of features of the invention described before or below with respect to the embodiments, which are not explicitly mentioned. In particular, the skilled person will thereby also add individual aspects as improvements or additions to the respective basic embodiment of the present invention.

BRIEF DESCRIPTION OF THE DRAWINGS

The present invention is explained in more detail below with reference to the embodiments indicated in the schematic figures of the drawing, wherein.

Figure 1:
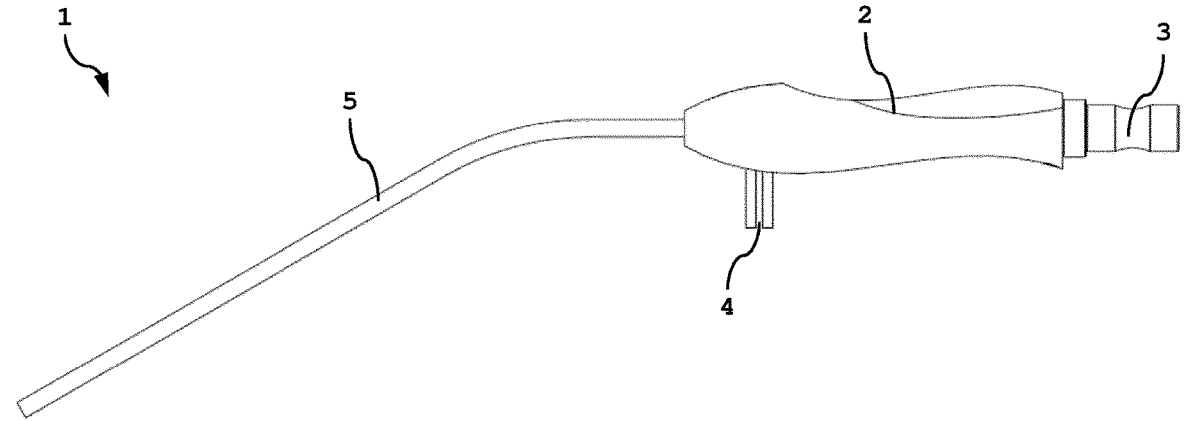
FIG. 1 shows a schematic view of the suction instrument according to the first aspect of the present invention.

The accompanying figures of the drawing are intended to provide a further understanding of the exemplary embodiments of the invention. The embodiments illustrate exemplary embodiments and, in connection with the description, serve to explain principles and concepts of the invention. Other embodiments and many of the advantages mentioned will be apparent with reference to the drawings. The elements of the drawings are not necessarily shown to scale with respect to each other.

In the figures of the drawing, elements, features and components, which are the same, have the same function and act in the same way, are each given the same reference numerals, unless otherwise stated.

DESCRIPTION OF EXEMPLARY EMBODIMENTS

In FIG. 1, the suction instrument 1, in this case a bipolar mapping suction instrument, is schematically shown according to the first aspect of the present invention. The suction instrument 1 comprises a handpiece 2, a first interface 3, a second interface 4 and a cannula unit 5.

The handpiece 2 is ergonomically shaped and made of plastic (e.g., poyetheretherketone, PEEK, PC/ABS). A surgeon can take the handpiece 2 in his hand and guide the suction instrument 1 over it during a surgical procedure.

The first interface 3 is formed as a fluid-conducting coupling for a semirigid tube (not shown) at a proximal end of the handpiece 2. Both a suction instrument (not shown) and an rinsing device (not shown) can be fluidly connected to the first interface 3 by means of the semirigid tubing.

The second interface 4 is formed as two connector pins distally on a bottom surface of the handpiece 2, to which a bipolar cable (not shown) can be connected, and comprises a bipolar connection. A stimulation device (not shown) may be electrically connected to the second interface 4 by means of the bipolar cable, and may thus connected in a bipolar fashion. Alternatively, a monopolar cable may be connected to one of the connection pins.

The cannula unit 5 has its proximal end firmly mechanically connected to the handpiece 2. The cannula unit 5 extends towards a tip or distal end of the cannula unit 5. Thereby, the cannula unit 5 has an angulation in a proximal area of the cannula unit 5 of 30° downwards.

Figure 2:
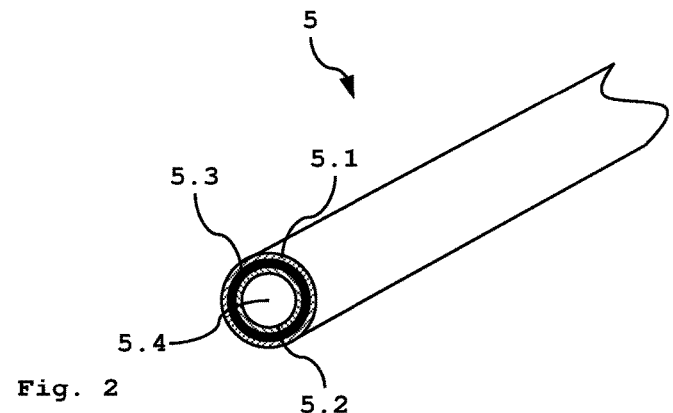
FIG. 2 shows an enlarged schematic view of the cannula unit of the suction instrument of FIG. 1.

The exact structure of the cannula unit 5 is shown schematically in FIG. 2. The cannula unit 5 comprises an outer cannula tube 5.1, an inner cannula tube 5.2 and an insulation 5.3.

The outer cannula tube 5.1 is formed of stainless steel, and is detachably firmly mechanically connected to the handpiece 2 (e.g., screw connection, snap connection, etc.). The outer cannula tube extends from the handpiece 2 to the tip of the cannula unit 5. Furthermore, the outer cannula tube 5.1 is mechanically connected to the handpiece 2 and electrically connected to one pole of the bipolar connection of the second interface 4 and thus to the stimulation device by means of an electrical contact, for example a solder joint or weld, in the handpiece 2. Thus, the outer cannula tube 5.1, in particular at the tip of the cannula unit 5, can be used as an electrode for monopolar or bipolar stimulation of tissue by the stimulation device.

The inner cannula tube 5.2 is formed of stainless steel and extends concentrically to the outer cannula tube 5.1, with the inner cannula tube 5.2 extending from the tip of the cannula unit 5 to beyond a proximal end of the outer cannula tube 5.1 into the handpiece 2. The inner cannula tube 5.2 is mechanically connected to the handpiece 2 and electrically connected to the corresponding other pole of the bipolar connection of the second interface 4 and thus to the stimulation device by means of an electrical contact, for example a solder joint or weld, in the handpiece 2. Thus, the inner cannula tube 5.2 can be used as an electrode for monopolar or bipolar stimulation of tissue by the stimulation device.

Insulation 5.3 is formed as a tube of polyamide, and insulates the outer cannula tube 5.1 over its entire length from the inner cannula tube 5.2 extending concentrically therein, thereby preventing an electrical short circuit between the two cannula tubes 5.1, 5.2 and enabling bipolar stimulation of tissue by the control device.

The inner cannula tube 5.2 has a lumen 5.4 extending from the tip of the cannula unit 5 to a distal end of the inner cannula tube 5.2. The lumen 5.4 of the inner cannula tube 5.2 is mechanically connected within the handpiece 2 and thereby fluidly connected to the first interface 3 and thus to the suction device and the rinsing device. The interior of the handpiece 2 may be formed in two parts, such that a first cavity (not shown) is separated from a second cavity (not shown) by a partition (not shown) up to the beginning of the inner cannula tube 5.2. For example, the suction instrument may be fluidly connected to the first cavity, while the rinsing device may be fluidly connected to the second cavity. Through the suction instrument, a negative pressure or vacuum can thus be applied to the lumen 5.4 of the inner cannula tube 5.2, so that a suction effect is created at the tip of the cannula unit 5, with which fluids such as blood and tissue can be sucked out of the situs. Analogously, the rinsing device can thus convey a rinsing medium such as isotonic saline solution to the tip of the cannula unit 5 and the situs can be rinsed or moistened with it. The rinsing medium from the rinsing device can then be sucked out of the situs by the suction instrument at the tip of the cannula unit 5.

Figure 3:
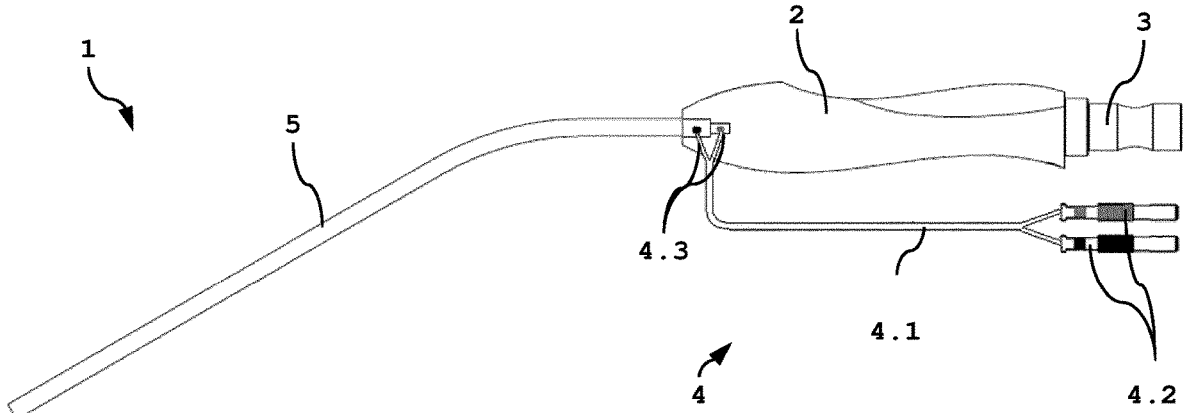
FIG. 3 shows a schematic view of a further embodiment of the suction instrument according to the first aspect of the present invention.

In FIG. 3, a further embodiment of the suction instrument 1 according to the first aspect of the present invention is schematically shown. The suction instrument 1 of FIG. 3 largely corresponds to the suction instrument 1 of FIG. 1. Therefore, only the differences are explained below.

Instead of two connection pins, the second interface 4 is configured here as a bipolar cable 4.1. The bipolar cable 4.1 has two sockets 4.2 or alternatively two plugs at its free end, which can be connected directly to an IOM system, more precisely to the stimulation device. The bipolar cable 4.1 is firmly integrated into the handpiece 2 and electrically connected to the outer cannula tube 5.1 and the inner cannula tube 5.2, respectively, by two electrical contacts 4.3 (e.g., soldered or welded joint).

Figure 4:
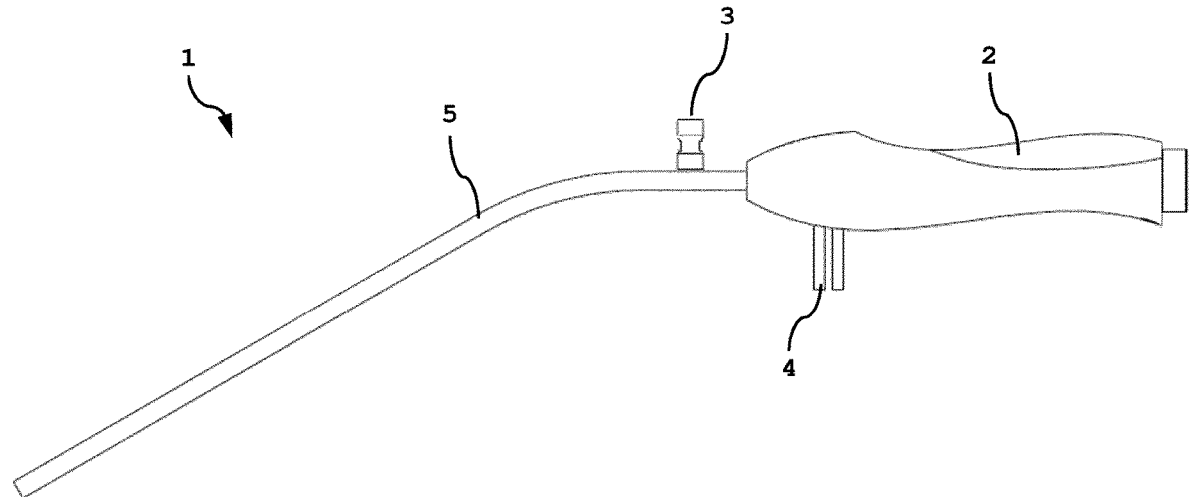
FIG. 4 shows a schematic view of a further embodiment of the suction instrument according to the first aspect of the present invention.

In FIG. 4, a further embodiment of the suction instrument 1 according to the first aspect of the present invention is schematically shown. The suction instrument 1 of FIG. 4 largely corresponds to the suction instrument 1 of FIG. 1 and FIG. 3. Therefore, only the differences are explained below.

The first interface 3 and the second interface 4 are arranged here directly on the cannula unit 5 instead of on the handpiece 2, or are formed integrally/integrally therewith. The second interface 4 can be implemented either by two connection pins as shown or alternatively by a bipolar cable 4.1, as described for the embodiment in FIG. 3. In each case, only one of the two interfaces 3, 4 can also be arranged directly on the cannula unit 5 and the other of the two interfaces 3, 4 can be arranged on the handpiece 2 in accordance with the embodiment examples from FIG. 1 and FIG. 3.

Figure 5:
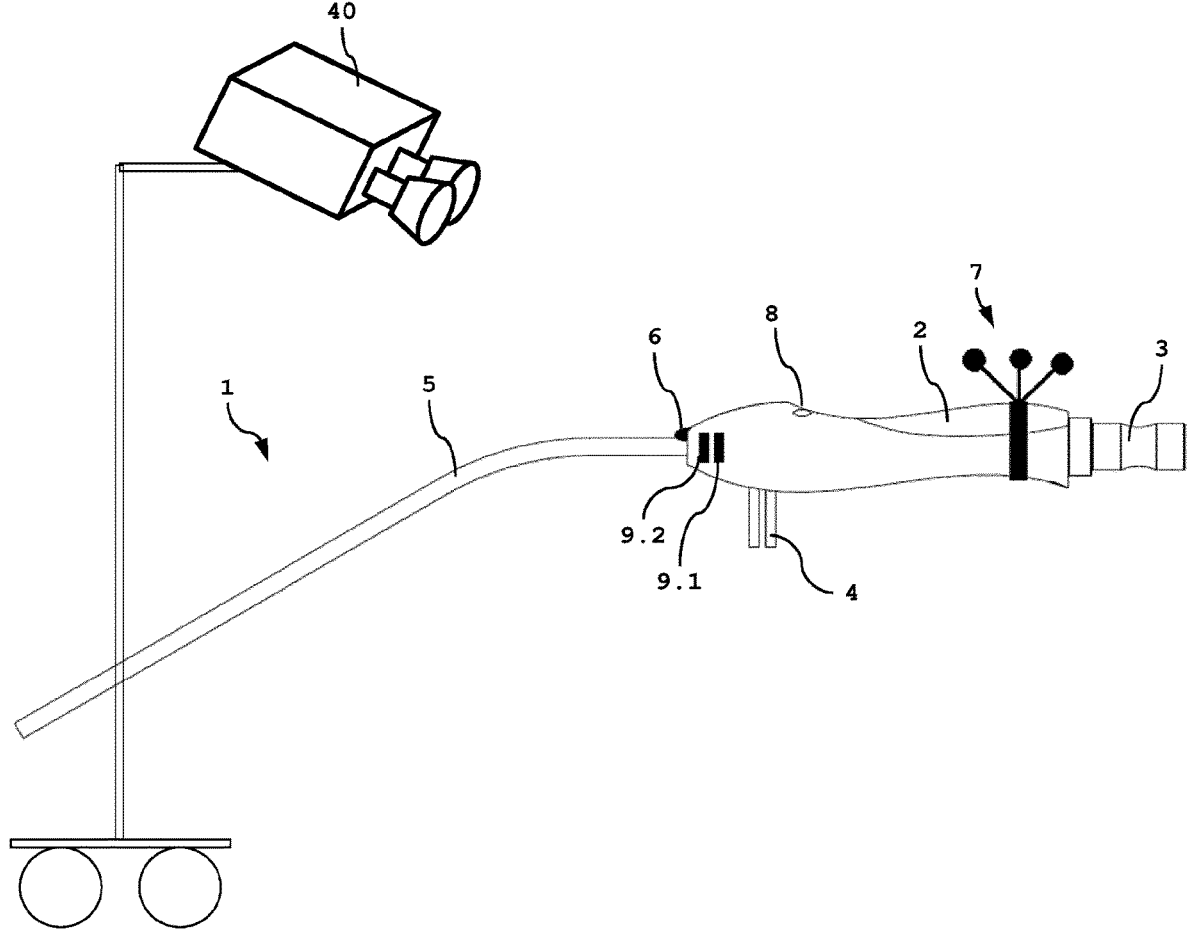
FIG. 5 shows a schematic view of a further embodiment of the suction instrument according to the first aspect of the present invention.

In FIG. 5, a further embodiment of the suction instrument 1 according to the first aspect of the present invention is schematically shown. The suction instrument 1 of FIG. 5 largely corresponds to the suction instrument 1 of FIG. 1, FIG. 3 and FIG. 4. Therefore, only the differences are explained below.

The suction instrument 1 here further comprises an LED 6, a tracking element 7, a suction control opening 8, a first operating element 9.1 and a second operating element 9.2.

The LED 6 is integrated into the handpiece 2. The LED 6 can be switched on and off either directly on the handpiece 2 or by means of the stimulation device. The LED 6 can alternatively be connected to a light guide (not shown) that extends along the outer tube surface of the outer cannula tube 5.1, where it can illuminate the situs. The light guides transmit the light emitted from a light source or from the LED and illuminate the situs.

The tracking element 7 is arranged here at the proximal end of the handpiece 2.

Alternatively, it may also be arranged at the proximal end of the cannula unit 5. Exemplarily, the tracking element 7 here has three markers in the form of reflective spheres arranged in a predetermined unequal-sided triangle with respect to each other. The position and pose of the tracking element 7 can be determined by an external navigation device 40 with a stereo camera by triangulation. From this, the position and pose of the suction instrument 1 and in particular the tip of the cannula unit 5 can be displayed in registered image data of the patient.

The suction control opening 8 is arranged on an upper side of the handpiece 2 and is fluidly connected to the lumen 5.4 of the inner cannula tube 5.2 through fluid channels in the handpiece 2. The suction opening 8 can be closed with a thumb, which allows the suction effect at the tip of the cannula unit 5 to be controlled.

The first operating element 9.1 is configured as a switch and is arranged on the handpiece 2 or alternatively on the suction instrument or rinsing device (not shown) or alternatively on the fluid-conducting cable or alternatively on the cannula unit 5. By means of the first operating element 9.1, for example, a first controllable valve (not shown) as well as a second controllable valve (not shown), which can be arranged in the handpiece 2 preferably directly at the first interface 3, can be opened and closed in opposite directions. The first controllable valve can fluidly connect the lumen 5.4 of the inner cannula tube 5.2 with the first interface 3 and thereabove with the suction instrument. The second controllable valve can fluidly connect the lumen 5.4 of the inner cannula tube 5.2 to the first interface 3 and above to the rinsing device. If the first controllable valve is opened by means of the first operating element 9.1 in a first position and the second controllable valve is closed at the same time, a negative pressure can be applied to the tip of the cannula unit 5 by means of the suction instrument and fluid and tissue can be aspirated from the situs. If the first controllable valve is closed in a second position by means of the first operating element 9.1 and the second controllable valve is open at the same time, the rinsing medium can be conveyed to the tip of the cannula unit 5 by means of the rinsing device and the situs can be rinsed or moistened. Optionally, the operating element 9.1 can also be moved to a third position in which both controllable valves are closed.

The second operating element 9.2 is configured as a switch and is arranged on the handpiece 2. The second operating element 9.2 is used to switch between monopolar operation and bipolar operation. For this purpose, the second operating element 9.2 is communicatively connected to the stimulation device by means of the second interface 4. In a first position of the second operating element 9.2, the control device is caused to operate in bipolar mode and to stimulate tissue by means of both cannula tubes 5.2 and 5.1, the stimulus response of the stimulated tissue being detected by means of corresponding conductive electrodes on the patient (not shown). In a second position of the second operating element 9.2, the stimulation device is caused to operate in monopolar mode and to electrically stimulate tissue through, for example, the inner cannula tube 5.2, further requiring the attachment of a counter electrode to the patient (not shown). The stimulus response of the stimulated tissue can then be detected by means of at least one, preferably two, conductive electrodes on the patient (not shown). In a third position of the second operating element 9.2, no stimulation takes place and only a separate rinsing or suction process can be performed.

Figure 6:
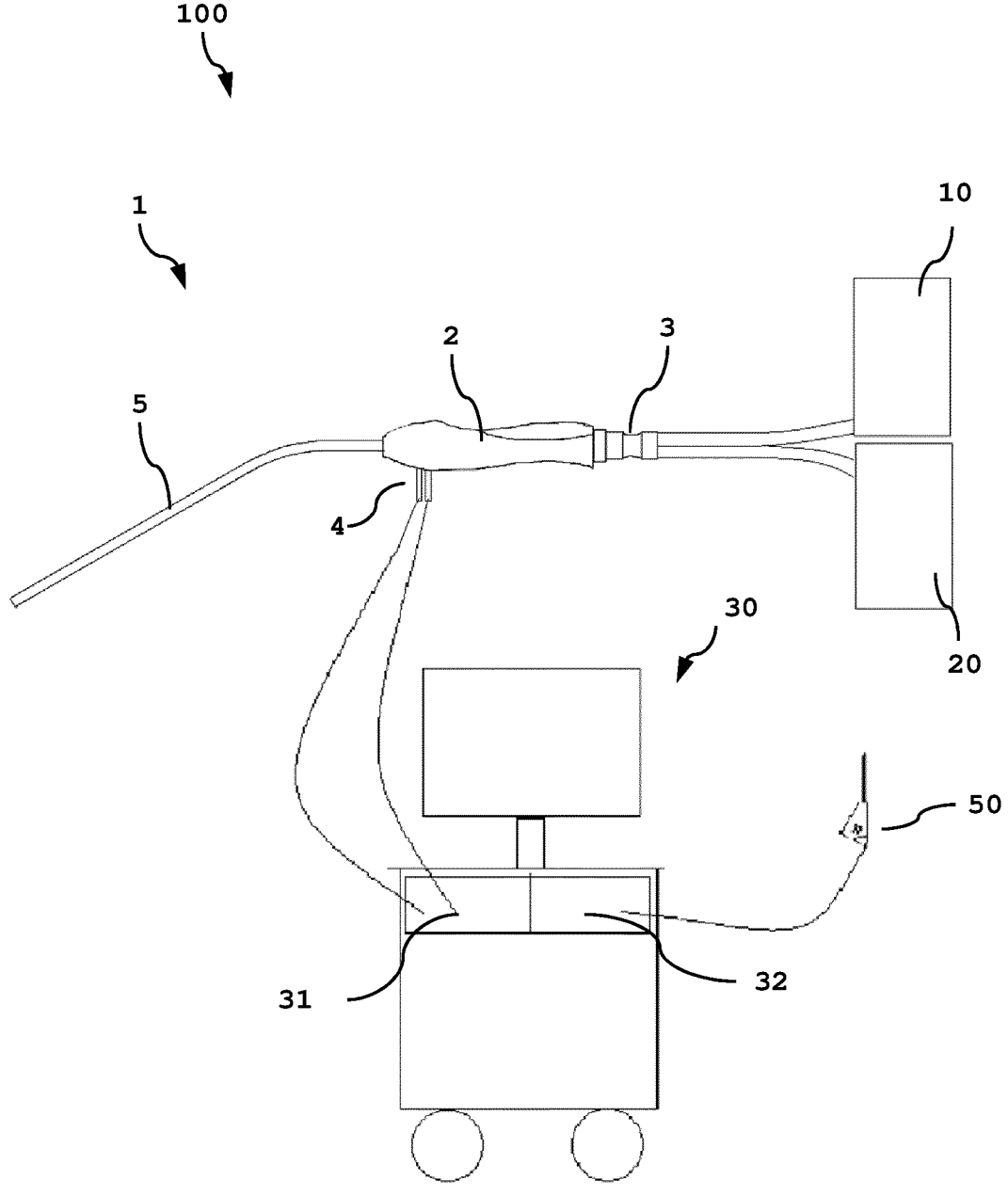
FIG. 6 shows a schematic view of the system according to the second aspect of the present invention.

FIG. 6 schematically illustrates the system 100 for aspirating fluids and tissue and monitoring nerve tissue according to the second aspect of the present invention. The system 100 comprises one of the suction instruments 1 of FIGS. 1 to 5 according to the first aspect of the present invention, as well as the suction instrument 10, the rinsing device 20, an IOM system 30 and at least one, preferably two, additional conductive electrodes 50 (for clarity, only one conductive electrode is shown).

The IOM system 30 may be a control device comprising a data processing device (e.g., computer, laptop, etc.). The IOM system 30 includes a stimulation device 31 and a monitoring device 32 communicatively connected to the stimulation device 31. The stimulation device 31 and the monitoring device 32 may be integrated as separate hardware modules in the IOM system 30, or implemented as software modules in the IOM system 30.

The suction instrument 1 is fluidly connected to both the suction instrument 10 and the rinsing device 20 at the first interface 3 by means of a semirigid tube, exemplarily comprising two separate fluid lines. Further, at the second interface 4, the suction instrument 1 is electrically connected to the IOM system 30 or directly to the stimulation device 31 by means of a bipolar cable.

If bipolar operation is selected (for example, by means of the second operating element, not shown here), the stimulation device 31 can electrically stimulate tissue that is touched with the tip of the cannula unit 5 by means of both cannula tubes 5.1 and 5.2. The stimulation response of the stimulated tissue is detected by means of one, preferably two, additional conductive electrodes 50 attached to the patient (executed here as a needle electrode) and passed on to the monitoring device 32 as a conductive signal. The derivative signal may be amplified by an amplifier (analog or digital, not shown) and/or filtered by a filter device (not shown). The user, for example a surgeon, and alternatively or additionally the monitoring device 32 monitor the reject signal and compare it to predefined thresholds. The monitoring device 32 may output the detection signal and additionally a warning signal, if a limit value is exceeded, visually by means of a screen (not shown) and/or acoustically by means of a loudspeaker (not shown).

The conductive electrodes 50, here needle electrodes or alternatively surface electrodes, are electrically connected to the IOM system 30, or are directly connected to the monitoring device 32 by means of cables.

Provided that the stimulation device 31 is set to monopolar operation, tissue in the situs is stimulated, for example, by means of the inner cannula tube 5.2 and an additional counter electrode (not shown) attached to the patient and electrically connected to the stimulation device 31 or the IOM system 30, and the stimulus response of the stimulated tissue is detected by means of the conductive electrodes 50. The detected stimulus response is passed to the monitoring device 32 as a reject signal. The reject signal may be amplified by an amplifier (analog or digital, not shown) and additionally or alternatively filtered by a filter device (not shown). The user, for example a surgeon, and alternatively or additionally the monitoring unit 32 monitor the reject signal and compare it to predefined threshold values. The monitoring unit 32 may output the reject signal and a warning signal, if a limit value is exceeded, visually by means of a display screen (not shown) and/or acoustically by means of a loudspeaker (not shown).

Before performing, for example, a tumor resection in the brain, the suction instrument 1 is connected to the IOM system 30 or directly to the stimulation device 31 by means of the bipolar cable. The conduction takes place by means of additionally inserted conduction electrodes 50 in (needle electrode) or on (surface electrode) muscles. Preferably, different muscles of the upper extremities or the head are selected and provided with several conductive electrodes 50. During tumor resection in the brain, the tip of the cannula unit 5 is placed at the site to be resected and the tissue at the tip of the cannula unit 5 between the inner cannula tube 5.2 and the outer cannula tube 5.1 is electrically stimulated by adding current to the inner cannula tube 5.2. A check is made to see whether or not the stimulation triggers an MEP (motor evoked potential) at this location. If no MEP is elicited on the motor cortex, it is tumorous tissue that can be resected, whereas successful MEP derivation indicates that it is func- tionally relevant tissue and stimulation and resection should be continued at another site. Monopolar stimulation is performed by means of one of the two stimulation poles on the cannula unit 5, preferably the inner cannula tube 5.2, and an additional counter electrode inserted on the patient. The conductive electrodes 50 are placed according to the bipolar stimulation. In the present case, the monopolar stimulation can also serve as a distance radar. Depending on the stimu- lation intensity, it can be estimated at what distance the motor pathways are arranged. Here, a rule of thumb of 1 mA per 1 mm applies. This means that successful MEP stimu- lation at 5 mA indicates that the pyramidal tract is approxi- mately 5 mm away. The tip of the cannula unit 5 can be at the tissue under examination at any time during critical phases of the procedure and stimulate it continuously (con- tinuous subcortical mapping). Fluids and tumor tissue are aspirated through the lumen 5.4 of the inner cannula tube 5.2 without damaging the patient's nearby nerve tracts. Serious consequences such as deficits and paralysis are avoided for the most part.

The following example serves to illustrate the present invention without limiting its scope.

The subject is the removal of a vestibular schwannoma, which is also called acoustic neuroma (AKN). Vestibular schwannoma is a tumor that originates from the vestibulo- cochlear nerve sheath and is directly adjacent to this nerve. The vestibulocochlear nerve is a cranial nerve responsible for hearing and balance function. Classic complaints of patients with vestibular schwannoma are dizziness, hearing loss and tinnitus. Pronounced vestibular schwannomas can also affect the function of the facial nerve. Removal of an AKN is performed in neurosurgery with the use of intraop- erative neuromonitoring. Essential here is the monitoring of auditory function by means of acoustic evoked potentials and of facial nerve function by means of electromyographic (EMG) measurement. Electrical stimulation is also used in this context. In the case of extensive tumors, monitoring of other cranial nerves (e.g., the trigeminal nerve and caudal cranial nerves) by EMG may be advisable.

In this case, suction instrument 1 or the bipolar mapping suction instrument is used for direct stimulation of the facial nerve or the other cranial nerves. Both bipolar and monopolar stimulation can be used here, which means that the conductive electrodes 50 are placed near the situs. The two connection pins of the second interface 4 of the suction instrument 1 are connected to the stimulation device 31 of the IOM system 30 by means of a bipolar cable with touch proof sockets. The handpiece 2 of the suction instrument 1 is fluidly connected to a suction instrument 10 with a semirigid tube at the first interface 3. In this case, the conductive electrodes 50 are placed in the target muscles of the cranial nerves. In the case of the facial nerve, for example, this is predominantly the mimic muscles of the face.

After access has been gained through skin incision and craniotomy behind the ear, the general function of the facial nerve can be estimated by means of monopolar stimulation, which is activated either by the second operating element 9.2 (switch) on the handpiece 2 or disconnection of one of the sockets of the bipolar cable, as well as an approximate determination of the distance to the nerve by stimulation threshold determination.

During stimulation, a monitor of the IOM System 30 displays the stimulus response in real time for interpretation and acoustically indicates it by means of a loudspeaker. At the same time, aspiration of fluids or tissue can be performed with the same instrument. In the further course of the operation, when this is performed in the direct vicinity of the cranial nerves, the system is switched to the bipolar function (by means of the second operating element 9.2 (switch) on the handpiece 2 or connection of the second socket of the bipolar cable to the second interface 4). Now the individual cranial nerves can be identified very selectively by bipolar stimulation. Continuous mapping allows the surgeon to know exactly where the cranial nerves and tumor are arranged, allowing for better targeted nerve sparing. Once a stimulus response is triggered, it is healthy and functional nerve tissue. If, on the other hand, no stimulus response is triggered, it is tumorous tissue that is to be resected. The fact that the suction instrument and the stimulation probe are combined in the suction instrument 1 or the bipolar mapping suction instrument allows close monitoring of the nerves and control of their function, as there is no need to change instruments. Additionally or alternatively, impedance spec- troscopy can be used to differentiate tumor tissue from healthy tissue by measuring the impedance of the tissue surrounding the tip of the cannula tube 5.

To prevent the situs from drying out or surgical residues from drying on, the suction instrument 1 can also be used to flush the situs. The rinsing fluids and the tissue residues can then be aspirated with the suction instrument 1. The suction process or the suction strength can be controlled with the suction control opening 8 on the handpiece 2.

Light is emitted from the handpiece 2 or alternatively from the tip of the cannula unit 5 by means of an LED or a light guide. This provides additional illumination of the operating area. Optionally, the tracking element 7 can addi- tionally be plugged onto the handpiece 2. Cameras of the navigation system 40 can then determine the current position and pose of the suction instrument 1 and track it. This offers significant advantages, particularly in neurosurgery and spi- nal surgery, such as increased precision and orientation during minimally invasive surgical procedures.

The main advantage of the suction instrument 1 or the bipolar mapping suction instrument is thus that it is no longer necessary to change instruments in a cumbersome manner. The suction instrument 1 combines a suction instru- ment with two stimulation contacts. The goal of complete tumor resection without damaging nearby nerve tracts is supported and simplified with the suction instrument 1. Furthermore, the surgical time is shortened by avoiding the need to change instruments. Bipolar stimulation also enables focused and selective stimulation and identification of nerve pathways, and the switching function between bipolar operation and monopolar operation enables the two methods to be merged into one instrument.

Although the present invention has been fully described above with reference to preferred embodiments, it is not limited thereto, but is modifiable in a variety of ways.

LIST OF REFERENCE NUMERALS

1 Suction instrument
2 Handpiece
3 First interface
4 Second interface
4.1 Bipolar cable
4.2 Sockets
4.3 Electrical contact
5 Cannula unit
5.1 Outer cannula tube
5.2 Inner cannula tube
5.3 Insulation
6 LED
7 Tracking element
8 Suction control opening
9.1 First operating element
9.2 Second operating element
10 Suction instrument
20 Rinsing device
30 IOM system
31 Stimulation device
32 Monitoring device
40 Navigation device
50 Deflecting electrode

The invention claimed is:

1. A method for using a suction instrument for surgical purposes, the method comprising:

holding a handpiece and using the handpiece to guide the suction instrument;

using a first interface to establish at least one fluid connection with an external suction device or rinsing device;

applying, using the external suction device and via the first interface, negative pressure to a cannula unit extending from the handpiece to aspirate fluids from a surgical site, the cannula unit including an electrically conductive outer cannula tube, an electrically conductive inner cannula tube concentrically arranged in the outer cannula tube, the inner cannula tube forming a lumen capable of conducting fluids, tissue, or gases;

using a second interface to establish a bipolar electrical connection with an external stimulation device; and using the cannula unit extending from the handpiece in an axial direction and mechanically connected to the handpiece at a proximal end of the cannula unit to perform intraoperative neuromonitoring (IONM), wherein using the cannula unit comprises applying, using the electrical stimulation device and via at least one of the inner and outer cannula tubes, electrical stimulation to nervous tissue of a subject and monitoring a response of the subject and wherein:

the electrically conductive inner cannula tube is electrically connected to a first pole of the bipolar electrical connection of the second interface, and fluidly connected to the first interface;

the electrically conductive outer cannula tube electrically connected to a second pole of the bipolar electrical connection of the second interface; and the cannula unit includes insulation concentrically arranged between the outer cannula tube and the inner cannula tube and configured to fully electrically insulate the outer cannula tube and the inner cannula tube in relation to one another.

2. The method of claim 1, further comprising providing an illumination device comprising at least one of a light source and a light guide, wherein the light outlet is arranged on the handpiece or alternatively on the cannula unit and is configured to allow light to exit from the light guide or alternatively from the light source in the direction of a situs, wherein the light guide is configured to guide light emitted from the light source or alternatively from an external light source to the light outlet.

3. The method of claim 1, further comprising providing a tracking element configured to be detected by an external navigation device and fixedly or detachably mechanically connected to the handpiece or the cannula unit.

4. The method of claim 1, wherein at least one of the outer cannula tube, the inner cannula tube and the insulation are made biocompatible or bioinert.

5. The method of claim 4, wherein at least one of the outer cannula tube and the inner cannula tube are made of stainless steel.

6. The method of claim 4, wherein the insulation is made of plastic or polyamide.

7. The method of claim 1, wherein the cannula unit has an outer diameter of 1 millimeter (mm) to 15 mm.

8. The method of claim 1, wherein the cannula unit has a length of 10 centimeters (cm) to 40 cm.

9. The method of claim 1, wherein the cannula unit is straight or alternatively has a bend with an angle of 10° to 60° or with an angle of, 30° in a proximal region.

10. The method of claim 1, wherein the handpiece comprises a suction control opening which is fluidly connected to the inner cannula tube.

11. The method of claim 1, wherein the cannula unit is fixedly or detachably mechanically connected to the handpiece at the proximal end of the cannula unit.

12. The method of claim 1, further comprising providing a first controllable valve, wherein the inner cannula tube is fluidly connected to the external suction device by means of the first controllable valve and a first fluid connection of the first interface.

13. The method of claim 12, wherein the handpiece further comprises a first operating element which is configured to switch between a suction function of the external suction device and a rinsing function of the external rinsing device.

14. The method of claim 12, further comprising a second controllable valve, wherein the inner cannula tube is fluidly connected to the external rinsing device by means of the second controllable valve and a second fluid connection of the first interface.

15. The method of claim 1, wherein the second interface comprises two connection pins for establishing a monopolar or bipolar connection.

16. The method of claim 1, wherein the handpiece further comprises a second operating element, wherein the second interface is further configured to establish a communicative connection of the second operating element with the external stimulation device, and wherein the second operating element is configured to switch between a monopolar operation and a bipolar operation.

17. The method of claim 1, wherein the second interface comprises a bipolar cable for establishing the monopolar or bipolar electrical connection.

* * * * *